US008883831B2

(12) United States Patent
Bear et al.

(10) Patent No.: US 8,883,831 B2
(45) Date of Patent: Nov. 11, 2014

(54) COMPOSITIONS AND METHODS FOR MINIMIZING OR REVERSING AGONIST-INDUCED DESENSITIZATION

(71) Applicant: PharmoRx Therapeutics, Inc., Westborough, MA (US)

(72) Inventors: David M. Bear, Weston, MA (US); Robert M. Kessler, Nashville, TN (US)

(73) Assignee: PharmoRx Therapeutics, Inc., Westborough, MA (US)

( * ) Notice: Subject to any disclaimer, the term of this patent is extended or adjusted under 35 U.S.C. 154(b) by 0 days.

(21) Appl. No.: 13/758,569

(22) Filed: Feb. 4, 2013

(65) Prior Publication Data

US 2013/0190343 A1 Jul. 25, 2013

Related U.S. Application Data

(62) Division of application No. 12/603,235, filed on Oct. 21, 2009, now abandoned.

(60) Provisional application No. 61/111,455, filed on Nov. 5, 2008.

(51) Int. Cl.
| | | |
|---|---|---|
| *A01N 43/78* | (2006.01) | |
| *A61K 31/485* | (2006.01) | |
| *A61K 31/439* | (2006.01) | |
| *A61K 31/404* | (2006.01) | |
| *A61K 31/4045* | (2006.01) | |
| *A61K 31/428* | (2006.01) | |

(52) U.S. Cl.
CPC ............. *A61K 31/439* (2013.01); *A61K 31/485* (2013.01); *A61K 31/404* (2013.01); *A61K 31/4045* (2013.01); *A61K 31/428* (2013.01)
USPC ............................ 514/365; 514/367; 514/370

(58) Field of Classification Search
USPC .......................................... 514/365, 367, 370
See application file for complete search history.

(56) References Cited

U.S. PATENT DOCUMENTS

| | | |
|---|---|---|
| 5,512,593 A | 4/1996 | Dante |
| 5,817,665 A | 10/1998 | Dante |
| 5,958,962 A | 9/1999 | Cook |
| 6,001,848 A | 12/1999 | Noble |
| 6,001,861 A | 12/1999 | Oertel et al. |
| RE36,547 E | 2/2000 | Crain et al. |
| 6,716,854 B2 | 4/2004 | McBrinn et al. |
| 6,765,010 B2 | 7/2004 | Crain et al. |
| 2002/0156056 A1 | 10/2002 | Johnson |
| 2007/0099947 A1 | 5/2007 | Dean, III et al. |
| 2007/0179168 A1 | 8/2007 | Cowley et al. |
| 2008/0045610 A1 | 2/2008 | Michalow |

FOREIGN PATENT DOCUMENTS

WO    WO 00/03715    1/2000

OTHER PUBLICATIONS

Singh, Vijay Pal et al., "Paradoxical effects of opioid antagonist naloxone on SSRI-induced analgesia and tolerance in mice" Pharmacology Nov. 2003, vol. 69, No. 3, pp. 115-122 Abstract.
Balcells-Olivero, M. et al, "Naltrexone attenuates acute amphetamine-induced rearing and blocks its sensitization by repeated amphetamine" Society for Neuroscience Abstracts, vol. 22, No. 1-3, 1996, p. 78 Abstract.
Tiihonen et al. "A Comparison of Aripiprazole, Methylphenidate, and Placebo for Amphetamine Dependence" Am J Psychiatry 2007; 164:160-162. (3 pages).
Enz, Ralf. "The trick of the tail: protein-protein interactions of metabotrophic glutamate receptors" BioEssays 2006; 29:60-73. (14 pages).
Popowicz et al. "Filamins: promiscuous organizers of the cytoskeleton" TRENDS in Biochemical Sciences 2006; vol. 31(7). (9 pages).
Lin et al. "Dopamine D2 and D3 receptors are linked to the actin cytoskeleton via interaction with filamin A" PNAS 2001; 98(9): 5258-5263. <www.pnas.org/cgi/doi/10.1073/pnas.011538198> (6 pages).
Obadiah et al. "Adenylyl Cyclase Interaction with the D2 Dopamine Receptor Family; Differential Coupling to Gi, Gz and Gs" Cellular and Molecular Nuerobiology 1999; 19(5): 653-664. (12 pages).
Onoprishvili et al. "Interaction Between the u Opioid Receptor and Filamin A Is Involved in Receptor Regulation and Trafficking" Mol Pharmacol 2003; 64(5): 1092-1100. (9 pages).
Seck et al. "Binding of Filamin to the C-terminal Tail of the Calcitonin Receptor Controls Recycling" The Journal of Biological Chemistry 2003; 278(12): 10408-10416. (9 pages).
Largent-Milnes et al. "Oxycodone Plus Ultra-Low-Dose Naltrexone Attenuates Neuropathic Pain and Associated u-Opioid Receptor-Gs Coupling" The Journal of Pain 2008; 9(8): 700-713. (14 pages).

(Continued)

*Primary Examiner* — Renee Claytor
(74) *Attorney, Agent, or Firm* — Dean Farmer; Nathan W. Poulsen

(57) ABSTRACT

Methods and compositions are provided for preventing or reversing loss of the therapeutic effect of a drug, where the loss is associated with the repeated administration of the drug to a patient. The method includes administering to the patient a dopamine receptor agonist or partial agonist or a drug that increases the extracellular level of dopamine by enhancing release of dopamine, decreasing the removal of dopamine from the extracellular space, enhancing the synthesis of dopamine within the brain, or decreasing metabolic degradation of dopamine; and also administering to the patient an opioid receptor antagonist in an ultra-low dose amount, wherein the ultra-low dose amount is effective to prevent or reverse loss of therapeutic effects associated with the repeated administration of the drug to the patient. The methods are useful for various treatments, including treating Parkinson's Disease, Restless Leg Syndrome, depression, schizophrenia, psychostimulant drug abuse, or attention deficit disorder.

11 Claims, 3 Drawing Sheets

(56) References Cited

OTHER PUBLICATIONS

Huang et al. "The calcium-sensing receptor and its interacting proteins" J. Cell. Mol. 2007; 11(5): 923-934. (12 pages).

Thomas et al. "G Protein Coupling and Signaling Pathway Activation by M Muscarinic Acetylcholine Receptor Orthosteric and Allosteric Agaonists" The Journal of Pharmacology and Experimental Therapeutics 2008; 327 (2):365-374. (10 pages).

Onoprishvili et al. "Chronic morphine treatment up-regulates mu opioid receptor binding in cells lacking Filamin A" Brain Res. 2007; 1177: 9-18. (20 pages).

Scott et al. "Cooperative Regulation of Extracellular Signal-Regulated Kinase Activation and Cell Shape Change by Filamin A B-Arrestins" Molecular and Cellular Biology 2006; 26(9): 3432-3445. (14 pages).

Paulus et al. "Less is more: pathophysiology of dopaminergic-therapy-related augmentation in restless legs syndrome" Lancet Neurol 2006, 5: 878-886. (9 pages).

Wang et al. "High-Affinity Naloxone Binding to Filamin A prevents Mu Opioid Receptor-Gs Coupling Underlying Opioid Tolerance and Dependence" PLoS ONE 2008; 3(2): e1554. <www.doi:10.137/journal.pone.0001554> (10 pages).

Bartlett et al. "Dopamine responsiveness is regulated by targeted sorting of D2 receptors" PNAS 2005; 102(32): 11521-11526. <www.pnas.org/cgi/doi/10.1073/pnas.0502418102> (6 pages).

Cho et al. "Roles of Protein Kinase C and Actin-Binding Protein 280 in the Regulation of Intracellular Trafficking of Dopamine D3 Receptor" Molecular Endocrinology; 21(9): 2242-2254. (13 pages).

Kim et al. "Differential Regulation of the Dopamine D2 and D3 Receptors by G Protein-coupled Receptor Kinases and B-Arrestins" The Journal of Biological Chemistry 2001; 276(40): 37409-37414. (6 pages).

Wang et al. "Naloxone's Pentapeptide Binding Site on Filamin A Blocks Mu Opioid Receptor-Gs Coupling and CREB Activation of Acute Morphine" PLoS ONE 2009; 4(1): e4282. <www.doi:10.137/journal.pone.0004282> (11 pages).

Kim et al. "G Protein-coupled Receptor Kinase Regulates Dopamine D3 Receptor Signaling by Modulating the Stability of a Receptor Filamin-B-Arrestin Complex" The Journal of Biological Chemistry 2005; 280(13): 12774-12780. (7 pages).

Scott et al. "Placebo and Nocebo Effects Are Defined by Opposite Opioid and Dopaminergic Responses" Arch Gen Psychiatry; 65(2): 220-231. (12 pages).

Lidstone et al. "Understanding the Placebo Effect: Contributions from Neuroimaging" Mol Imaging Biol 2007; 9: 176-185. (10 pages).

Besson et al. "Dopaminergic and Opioidergic Mediations of Tricyclic Antidepressants in the Learned Helplessness Paradigm" Pharmacology Biochemistry and Behaviour 1999; 64(3): 541-548. (8 pages).

Amiaz et al. "Resolution of treatment-refractory depression with naltrxone augmentation of paroxetine—a case report" Psychopharmacology 1999; 143: 433-434. (2 pages).

Carlezon et al. "Depressive-Like Effects of the k-Opioid Receptor Agonist Salvinorin A on Behavior and Neurochemistry in Rats" The Journal of Pharmacology and Experimental Therapeutics 2006; 316(1): 440-447. (8 pages).

Schug, Stephan A. "The role of tramadol in current treatment strategies for musculoskeletal pain" Therapeutics and Clinical Risk Management 2007; 3(5): 717-723. (7 pages).

Paquette et al. "Cannabinoid-included tolerance is associated with a CB1 receptor G protein coupling switch that is prevented by ultra-low does rimonabant" Behavioural Pharmacology 2007; 18: 767-776. (11 pages).

Tribal et al. "Apomorphine in idiopathic restless legs syndrome: an exploratory study" J Neurosurg Psychiatry 2005; 76(2): 181-185. (6 pages).

COMPOSITIONS AND METHODS FOR MINIMIZING OR REVERSING AGONIST-INDUCED DESENSITIZATION

CROSS-REFERENCE TO RELATED APPLICATIONS

This application claims the benefit of U.S. Provisional Application No. 61/111,455, filed Nov. 5, 2008, which is incorporated by reference in its entirety.

FIELD

This disclosure is generally in the field of pharmaceutical formulations and drug therapies that involve minimizing or preventing desensitization of G protein coupled receptors.

BACKGROUND

Opioid antagonists, such as naltrexone and naloxone, are used in relatively high (i.e., milligram) doses for a variety of treatments including but not limited to eating disorders, narcotic dependence, and alcoholism. Treatment may involve administering the drug by oral tablet (e.g., REVIA™) or by parenteral injection, at doses in the range of 50 mg by tablet daily or 380 mg per month by intramuscular depot. U.S. Pat. No. 6,565,449 to Stinchcomb et al., describes the delivery of a prodrug of the opioid antagonist naltrexone and a transdermal delivery apparatus for same.

Dopamine is a neurotransmitter, or chemical messenger, that sends information to parts of the brain that control movement, coordination, cognitive functions, and emotions. There are five distinct dopamine receptors, which differ in terms of their pharmacological profiles and cellular distribution. The D2 receptor and the D3 receptor share many signaling pathways, are the main targets for most drugs used to treat extrapyramidal movement disorders as well as antipsychotic drugs, and are heavily expressed in the regions of the brain responsible for motor functions and emotional functions, respectively. In addition, some studies have shown that abnormal function of the D2 and D3 receptors are closely related to schizophrenia. Due to the critical role of these two dopamine receptors in terms of neurological function, many drugs have been used that target these receptors to affect dopamine related activity. However, the use of dopamine D2 and/or D3 receptor full and partial agonists in the treatment of neurological and psychiatric disorders is limited by desensitization of the dopamine D2 and/or D3 receptor induced by repeated use of such drugs, which undesirably can lead to a loss or diminution of therapeutic effects. The diminution in therapeutic effects may lead to the need for higher doses with the risk of untoward side effects. An unwanted loss of effect at the end of the dosing interval, as described by terms "wearing off" or "on-off", is thought to be a consequence of change in the constitutive activity of D2 and D3 receptors as discussed below.

Drugs which produce higher levels of extracellular dopamine also are used to treat neurological and psychiatric disorders, and can analogously produce dopamine D2 and/or D3 receptor desensitization. These agents increase extracellular dopamine levels by augmenting dopamine synthesis, by blocking reuptake of extracellular dopamine into dopamine neurons, by releasing dopamine from dopamine neurons, or by decreasing metabolic degradation of dopamine. Typically, drugs that increase extracellular dopamine levels have therapeutic effects which decrease with repeated administration or require higher doses of drugs, which may lead to side effects or a loss of the therapeutic properties of the drugs earlier in the dosing interval. This diminution or loss of therapeutic effects is likely related to desensitization of dopamine D2 and/or D3 receptors induced by chronic elevation of extracellular dopamine levels.

Parkinson's Disease occurs when a group of cells in the substansia nigra that produce dopamine begin to malfunction and die. As discussed above, dopamine is a neurotransmitter, or chemical messenger, that sends information to the parts of the brain that control movement and coordination. When a patient has Parkinson's Disease, his dopamine-producing cells begin to die, and therefore, the amount of dopamine produced in the brain decreases. Signals from the brain that tell the body how and when to move are therefore delivered more slowly, leaving a person incapable of initiating and controlling movements in a normal way. The four primary symptoms of Parkinson's Disease are tremor, or trembling in hands, arms, legs, jaw, and face; rigidity, or stiffness of the limbs and trunk, bradykinesia, or slowness of movement; and postural instability, or impaired balance and coordination. Other symptoms may include depression and other emotional changes; difficulty in swallowing, chewing, and speaking; urinary problems of constipation; skin problems; and sleep disruptions.

At present, there is no cure for Parkinson's Disease, but a variety of medications provide dramatic relief from the symptoms. Patients are often given levodopa (L-DOPA, 3,4-dihydroxy-L-phenylalanine) formulations including, but not limited to, combinations of levodopa with carbidopa (SINEMET™). Carbidopa delays the conversion of levodopa into dopamine until it reaches the brain. Nerve cells can use levodopa to make dopamine and replenish the brain's dwindling supply. Although levodopa helps many Parkinson's patients, not all symptoms respond equally to the drug. For example, bradykinesia and rigidity typically respond to this drug; however, tremor may only be marginally reduced and problems with balance and other symptoms may not be alleviated at all. Another typical therapy for Parkinson's Disease is the use of anticholinergic medications such as benztropine mesylate (COGENTIN™) and biperiden hydrochloride (AKINETON™) which block nerve impulses to help improve muscle control and which decrease levels of acetylcholine in order to achieve a closer balance with dopamine levels. Anticholinergic medications may only help control tremor and rigidity and not other associated symptoms. Other drugs referred to as dopamimetics including, but not limited to, bromocriptine, pergolide, pramipexole, and ropinirole, mimic the role of dopamine in the brain, causing the neurons to react as they would to dopamine. However, these dopamimetic drugs are not without undesirable side effects. It would be desirable to develop new or improved therapies for the treatment of Parkinson's Disease.

RLS is a neurological disorder characterized by unpleasant sensations in the legs and a strong urge to move when at rest in an effort to relieve these feelings. RLS sensations are often described by people as burning, creeping, tugging, or like insects crawling inside the legs. Often called paresthesias (abnormal sensations) or dysesthesias (unpleasant abnormal sensations), the sensations range in severity from uncomfortable to irritating to painful. Several prescription medications, most of which were developed to treat other diseases, are available to reduce the restlessness in the legs. These include medications for Parkinson's Disease, opioids, muscle relaxants, sleep medications, and medications for epilepsy.

Medications for Parkinson's Disease are the most common treatment for RLS. These medications include pramipexole (MIRAPEX™), pergolide (PERMAX™), ropinirole (REQUIP™), and a combination of carbidopa and levodopa (SINEMET™). However, as mentioned above, these medications have undesirable side effects including abrupt daytime sedation, on-off or wearing off effects, and tolerance requiring higher doses. Higher doses of the dopamimetics repinirole and pramipexole have been associated with compulsive gambling, inappropriate hypersexuality, and drowsiness which may occur suddenly during the day, potentially leading to adverse consequences, such as automobile accidents.

A common problem with the currently available dopamimetic treatments for RLS is tolerance. That is, a medication and dose that has previously been effective for relief of RLS symptoms becomes ineffective, or the symptoms return earlier. Tolerance leads to the use of higher doses of the medications, which increase the probability of unwanted side effects.

Major depressive disorder is a condition characterized by a pervasive low mood and loss of interest or pleasure in usual activities. The majority of currently used antidepressants target a limited number of neurotransmitter binding sites or transporters, particularly the serotonin transporter and serotonin receptors including 5HT2A and 5HT1A receptors, the norepinephrine transporter, the dopamine transporter and dopamine D2 and D3 receptors. Pharmacotherapy based on these agents fails to produce full remission in at least 30% of patients suffering major depressive episodes. Anhedonia, a global loss of pleasurable feelings, is a core symptom of depression and is believed to be mediated by decreased or abnormal dopamine neurotransmission in the limbic system, particularly the ventral striatum. A number of studies have implicated dysfunction of limbic dopaminergic neurotransmission in the etiology of anhedonia. There remains a significant need for new and improved antidepressant treatment for patients suffering from depression, especially refractory depression.

It also would be desirable to provide new or improved pharmaceutical formulations and methods for the treatment of symptoms associated with Parkinson's Disease, Restless Leg Syndrome, attention deficit disorder, schizophrenia, psychostimulant drug abuse, and other conditions for which augmentation of dopamine D2 and/or D3 neurotransmission is therapeutically beneficial that overcome the problems associated with the currently available treatments. In particular, it would be desirable to provide therapies that minimize or prevent desensitization to dopamine augmentation.

It would be desirable treat Parkinson's Disease, RLS, depression, particularly refractory depression, attention deficit disorder, schizophrenia, and psychostimulant drug abuse by modulating the dopamine system, increasing dopamine levels without causing tolerance or on-off effects. In particular, it would be desirable to prevent tolerance to the effects of drugs which directly stimulate dopamine D2 and D3 receptors or which elevate extracellular dopamine levels by modulating dopamine D2 and/or D3 receptor signaling.

SUMMARY

In one aspect, methods are provided for preventing or reversing loss of the therapeutic effect of a dopamine receptor agonist or partial agonist associated with the repeated administration of the dopamine receptor agonist or partial agonist to a patient. In one embodiment, the method includes administering to the patient (i) a dopamine receptor agonist or partial agonist, and (ii) an opioid receptor antagonist in an ultra-low dose amount, wherein the ultra-low dose amount is effective to prevent or reverse loss of therapeutic effects associated with the repeated administration of the dopamine receptor agonist or partial agonist to the patient. The opioid receptor antagonist may be selected, for example, from naloxone, naltrexone, diprenorphine, etorphine, dihydroetorphine, or a combination thereof.

In another aspect, methods are provided for preventing or reversing loss of the therapeutic effect of a drug associated with the repeated administration of the drug to a patient. In one embodiment, the method includes administering to the patient (i) a drug that increases the extracellular level of dopamine by enhancing release of dopamine, decreasing the removal of dopamine from the extracellular space, enhancing the synthesis of dopamine within the brain, and/or decreasing its metabolic degradation, and (ii) an opioid receptor antagonist in an ultra-low dose amount, wherein the ultra-low dose amount is effective to prevent or reverse loss of therapeutic effects associated with the repeated administration of the drug to the patient.

In still another aspect, pharmaceutical formulations are provided. In one embodiment, the formulation includes a dopamine receptor agonist or partial agonist, and an opioid receptor antagonist in an ultra-low dose amount. In another embodiment, the formulation includes an opioid receptor antagonist in an ultra-low dose amount and a drug that increases the extracellular level of dopamine by enhancing release of dopamine, by decreasing the removal of dopamine from the extracellular space, by enhancing the synthesis of dopamine within the brain, and/or by decreasing its metabolic degradation in the brain.

In yet another aspect, a method is provided for treating Restless Leg Syndrome, Parkinson's Disease, or another dopamine-related movement disorder in a patient. In one embodiment, the method includes administering to the patient a dopamine receptor agonist or partial agonist, and administering to the patient an opioid receptor antagonist in an ultra-low dose amount, wherein the dopamine receptor agonist or partial agonist is administered in an amount that is therapeutically effective when co-administered with the opioid receptor antagonist in an ultra-low dose amount.

In a further aspect, methods are provided for treating Parkinson's Disease in a patient. In one embodiment, the method includes administering to the patient a dopamine receptor against or partial agonist, levodopa, a monoamine oxidase inhibitor, a catechol-O-methyl transferase inhibitor, another drug decreasing the metabolic degradation of dopamine in the brain, or a combination thereof; and administering to the patient an opioid receptor antagonist in a ultra-low dose amount.

In still another aspect, methods are provided for treating depression in a patient. In one embodiment, the method includes administering to the patient a therapeutically effective amount of a dopamine agonist, a dopamine partial agonist, a dopamine reuptake inhibitor, a monoamine oxidase inhibitor, another drug decreasing the metabolic degradation of dopamine in the brain, a dopamine releasing drug, a selective serotonin dopamine reuptake inhibitor, a serotonin-norepinephrine reuptake inhibitor, or a serotonin-norepinephrine-dopamine reuptake inhibitor; and administering to the patient an opioid receptor antagonist in a ultra-low dose amount effective to prevent receptor desensitization in dopamine augmentation and/or to enhance antidepressant or to reduce restlessness.

In another aspect, methods are provided for treating schizophrenia in a patient. In one embodiment, the method includes administering to the patient a therapeutically effective amount of a partial dopamine agonist or a drug increasing extracellular dopamine levels, and administering to the patient an opioid receptor antagonist in a ultra-low dose amount of effective to prevent receptor desensitization in dopamine augmentation.

In still another aspect, methods are provided for treating psychostimulant abuse in a patient. In one embodiment, the method includes administering to the patient a therapeutically effective amount of a dopamine D2 and/or D3 agonist or partial agonist, a dopamine reuptake inhibitor, or a dopamine releasing drug; and administering to the patient an opioid receptor antagonist in an ultra-low dose amount effective to prevent receptor desensitization in dopamine augmentation.

In yet another aspect, methods are provided for treating attention deficit hyperactivity disorder (ADHD) in a patient. In one embodiment, the method includes administering to the patient a therapeutically effective amount of a drug that increases extracellular dopamine levels, and administering to the patient an opioid receptor antagonist in an ultra-low dose amount effective for receptor stabilization.

In a further aspect, methods are provided for treating a dopamine deficiency disease or condition in a patient. In one embodiment, the method includes administering to the patient a therapeutically effective amount of a dopamine D2 and/or D3 receptor agonist or partial agonist, or a drug increasing extracellular dopamine levels, and administering to the patient an opioid receptor antagonist in an ultra-low dose amount effective to prevent or reverse loss of therapeutic effects after repeated administration of the dopamine D2 and/or D3 receptor agonist or partial agonist or drug increasing extracellular dopamine levels.

In another aspect, methods are provided for the treatment of pituitary adenomas in a patient. In one embodiment, the method includes administering to the patient a therapeutically effective amount of a dopamine D2 agonist, and administering to the patient an opioid receptor antagonist in an ultra-low dose amount effective to reduce or prevent desensitization of dopamine D2 receptors.

In another aspect, treatment methods are provided that include identifying a patient having a condition selected from among Parkinson's Disease, Restless Leg Syndrome, depression, schizophrenia, and/or attention deficit disorder; and administering to the patient an opioid receptor antagonist in an ultra-low dose amount in combination with a non-opioid therapeutic.

DETAILED DESCRIPTION

Figure 1:
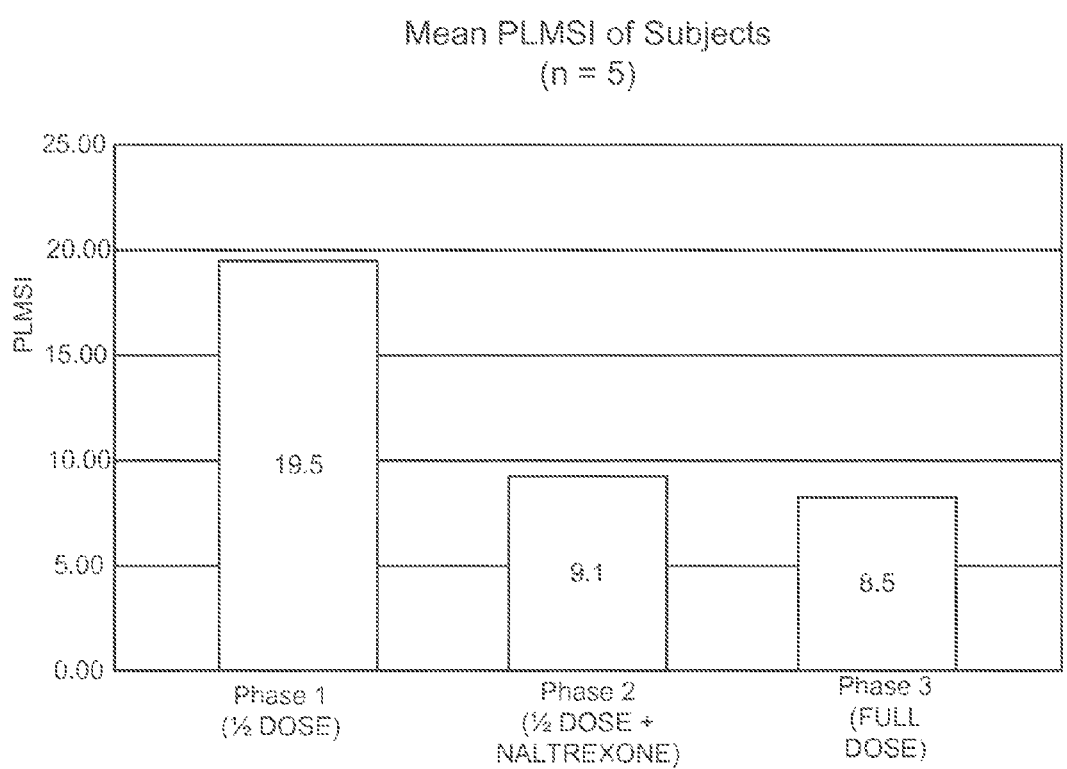
FIG. 1 is a bar graph, illustrating periodic limb movements (legs) in sleep index (PLMSI) measured in RLS subjects treated with a clinically effective "full" dosage of pramipexole or ropinirole, a half dosage of pramipexole or ropinirole, and half dosage of pramipexole or ropinirole in combination with ultra-low dose naltrexone (0.15 µg).

Methods are provided to minimize, at least partially reduce, or prevent desensitization of receptors in the situations discussed above, collectively referred to herein as therapeutic dopamine augmentation. Methods are also provided to minimize, at least that interact with Filamin A.

In one aspect, methods are provided to prevent desensitization to dopamine augmentation by administering a very low dose (ultra-low dose, ULD) of a mu opioid receptor antagonist. As used herein, the terms "mu opioid receptor antagonist" and "opioid receptor antagonist" are used interchangeable. Opioid receptor antagonists include, but are not limited to, naltrexone, naloxone, diprenorphine, etorphine, and dihydroetorphine. In preferred embodiments, these methods are used in the treatment of Parkinson's Disease, Restless Leg Syndrome, depression (e.g., refractory depression), attention deficit disorder, schizophrenia, and psychostimulant drug abuse. In one embodiment, these indications may be treated by administering to the patient an opioid receptor antagonist in and ultra-low dose amount in combination with a non-opioid therapeutic agent.

In one aspect, a method is provided for preventing or reversing loss of the therapeutic effect, i.e., desensitization, of a drug associated with the repeated administration of the drug to a patient. The method may include (a) administering to the patient a dopamine D2 and/or D3 receptor agonist or partial agonist, or a drug that increases the extracellular level of dopamine by (i) enhancing release of dopamine, (ii) decreasing the removal of dopamine from the extracellular space, (iii) enhancing the synthesis of dopamine within the brain, (iv) decreasing metabolic degradation of dopamine within the brain, or (v) a combination thereof; and (b) administering to the patient an opioid receptor antagonist in an ultra-low dose amount, wherein the ultra-low dose amount is effective to prevent or reverse loss of a therapeutic effect associated with the repeated administration of the drug to the patient.

In a preferred embodiment, the ultra-low dose of mu opioid receptor antagonist is administered to a patient in combination with a dopamimetic medication. Such co-administration of an ultra-low dose mu opioid receptor antagonist in dopamine receptors, allowing the dopamimetic drug to retain its therapeutic effects at lower doses (minimizing side effects of the dopamimetic) and over longer periods without abrupt Wearing off.

As used herein, the terms "preventing or reversing", "preventing or reducing", "prevent or reverse", and "prevent or reduce" used in describing the beneficial effect achieved with administration of the ULD mu opioid receptor include an at least partial reduction and/or an at least partial reversal of the described receptor desensitization. The terms include reducing, minimizing, at least partially preventing, and/or at least partially reversing the described receptor desensitization.

As used herein, the term "ultra-low dose" generally refers to dosages give to a patient that are less than 1.5 µg/kg (drug weight drug/patient weight). For depot injections, however, the ultra-low dose amount may comprise a dosage of about 0.1 ng/kg to 100 µg/kg. In some embodiments, receptor stabilization is achieved by co-administration of naltrexone in a dose between about 0.01 ng/kg and about 1.5 µg/kg, and more preferably between 0.0.1 ng/kg and about 150 ng/kg in certain embodiments. These dosages may administered one time per day, or 2 to 3 times daily. In some embodiments, one or both of the dosages are administered at night. Other dosing schedules are envisioned. For example, the dosages may be administered less frequently in extended release or controlled delivery formulations.

Such co-administration of the opioid antagonist with a dopamine D2 or D3 receptor agonist or partial agonist, or with a drug enhancing extracellular dopamine levels, will maintain and prevent loss of the therapeutic effects of the D2 and/or D3 receptor agonist or partial agonist drugs or the drug enhancing extracellular dopamine levels in the treatment of neurological and psychiatric disorders including, but not limited to, Restless Leg Syndrome, Parkinson's Disease, depression, attention deficit disorder, schizophrenia, and psychostimulant drug abuse.

As used herein, the terms "dopamine receptor agonist" and "dopamimetic" are used interchangeably, and refer to a dopamine D2 and/or D3 receptor full or partial agonist. Examples of dopamine receptor agonists include, but are not limited to, pramipexole, ropinirole, bromocriptine, pergolide, preclamol, talipexole, cabergoline, lisuride, roxindole, rotigotine, SDZ 208-911, SDZ 208-912, bifeprunox, aripiprazole, PD 158771, PD 128483, N-propylnorapomorphine, apomorphine, sumanirole, aplindore, BP897, CJB090, and RGH237, as well as other dopamine D2 and/or D3 agonists and partial agonists known in the art. It is understood that the methods described herein may also be used with dopamine receptor agonists which may be synthesized or identified later (e.g., a new chemical entity using methods known in the art of drug discovery.

Agents that increase extracellular dopamine levels by augmenting dopamine synthesis, by blocking reuptake of extracellular dopamine into dopamine neurons, or by releasing dopamine from dopamine neurons, include, but are not limited to, drug formulations containing L-DOPA; amphetamine formulations, including formulations of specific stereoisomers such as d-amphetamine; methylphenidate formulations, including formulations of specific stereoisomers; buproprion; serotonin dopamine reuptake inhibitors including but not limited to sertraline; serotonin norepinephrine reuptake inhibitors including but not limited to duloxetine, venlaxafin or desvenlafaxin, triple reuptake inhibitors such as JNJ 7925476, tesofensine, and DOV216303; selective norepinephrine reuptake inhibitors such as but not limited to atomoxetine formulations; as well as atypical antipsychotic drugs such as clozapine, ziprasidone, olanzapine, risperidone, and quetiapine, and the like. Non-limiting examples of drugs that increase the extracellular concentration of dopamine by decreasing metabolic degradation of dopamine include inhibitors of monoamine oxidase and catechol-O-methyl transferase. Examples of such inhibitors include, but are not limited to, phenelzine, tranylcypromine, selegiline, rasagiline, and tolcapone.

In various embodiments of the treatment methods described herein, the ultra-low dose of mu opioid receptor antagonist (or a metabolite therefore) may be administered to the patient by any of several suitable known oral or parenteral routes and dosages/delivery forms therefore. In one embodiment, oral administration may be by a pill, tablet or capsule containing a dopamimetic, dopamine reuptake blocker, or dopamine releasing drug in combination with an ultra low dose opioid antagonist. In one embodiment, the mu opioid receptor antagonist is delivered from a depot formulation for controlled, sustained release. For example, the depot may include a biodegradable matrix material (which may be a hydrogel) or a suspension of biodegradable polymeric microparticles, in which the mu opioid receptor antagonist is encapsulated or otherwise combined. These depots may be administered, for example, by injection, e.g., subcutaneous or intramuscular injection. Vivatrol (Cephalon Pharmaceuticals) is an FDA-approved example of the depot technology.

The dopamine receptor agonist or partial agonist, the drug enhancing extracellular dopamine levels, and the mu opioid receptor antagonist may be referred to herein individually as an "active agent" or collectively as the "active agents."

The dopamine D2 or D3 receptor agonist or partial agonist, or the drug enhancing extracellular dopamine levels, may be administered in the same or a different dosage form or delivery device, via the same or a different delivery route, as the mu opioid receptor antagonist. The delivery route may be oral or parenteral. Examples of suitable parenteral routes include topical (transdermal) and transmucosal (e.g., buccal) administration. The unit dosage form or forms containing one of active agents or both active agents may be an oral dosage form or parenteral dosage form. The oral dosage form may be a tablet or capsule. In one case, the active agent(s) may be formulated as a topical cream or gel. In another case, the active agents may be formulated for injection.

In still another case, the active agent(s) may be formulated and combined with a delivery device known in the art. Examples include devices for transdermal or subcutaneous administration of the agent(S), such as transdermal patches, microneedle arrays, patch pumps, infusion pumps, or the like. In another example, the device may be an implantable drug delivery device, such as an osmotic pump, a MEMs pump, or other pump, or another type of passively or actively controlled release device.

As used herein, the term "patient" includes mammals, such as humans, in need of medical treatment, including but limited to the treatment of management of diseases or conditions as described herein. The patient may be an adult or child.

While the observations, treatment methods, and pharmaceutical formulations described herein are not bound by any theory, the mechanisms described hereinbelow are proposed by which the ultra-low dose opioid receptor antagonists may exert their effect. Filamin A is a non-muscle, actin-binding, scaffolding protein which is found in the cytoplasm of CNS neurons. Filamin A appears to interact with the third intracellular loop of G protein coupled receptors (GPCRs) and to affect the coupling of these receptors to second messenger systems. GPCRs that are known to interact with Filamin A include the mu opioid receptor, dopamine D2 and D3 receptors, the calcium sensing receptor, the mGluR4, 5, 7 and 8 receptors, the muscarinic M1 receptor, and the calcitonin receptor.

Figure 2:
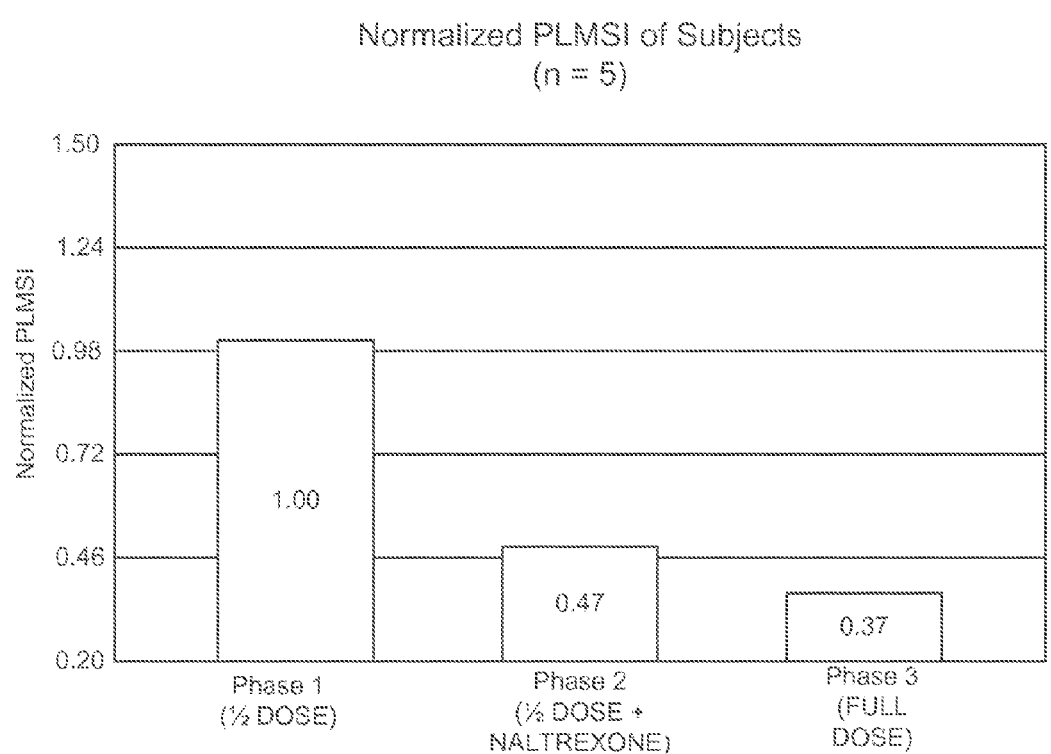
FIG. 2 is a bar graph, illustrating periodic limb movement normalized to the level seen in Phase 1, i.e. with a half dose treatment of dopamimetic.

Filamin A is required for normal receptor trafficking (i.e. externalization and internalization) in cells expressing dopamine D2 or D3 receptors, mu opioid receptors, calcitonin receptors, and other GPCR receptors that interact with Filamin A. Filamin A, GPCRs and β-arrestin form a complex required for G protein signaling and internalization of these receptors. Ultra-low dose naltrexone has been shown to bind with very high affinity (4 picomolar) to a pentapeptide segment at the carboxy terminal of Filamin A which modulates G protein signaling of mu opioid receptors. As illustrated in FIG. 2, it is believed that in Restless Leg Syndrome (RLS) the loss of therapeutic effects and augmentation of symptoms seen following chronic administration of dopamimetics is due to a loss of dopamine D2/3 receptor signaling with preservation of dopamine D1 receptor signaling. This is proposed to be due to differences in receptor internalization and recycling distinguishing these dopamine receptors.

With agonist stimulation, dopamine D2/3 receptors are internalized and degraded due to their interaction with G protein coupled receptor-associated sorting protein (GASP) leading to degradation of dopamine D2/3 receptors rather than recycling of these receptors to the membrane surface, which eventually produces prolonged decreases in membrane externalized dopamine D2/3 receptors. In contrast, dopamine D1 receptors which are internalized following dopamine D1 agonist stimulation do not interact with GASP and are efficiently recycled to the cell surface producing an increase in dopamine D1 versus D2/3 signaling.

One mechanism of prevention/reversal of desensitization of dopamine D2/3 receptors by ultra low dose naltrexone following chronic administration of dopamine D2 and D3 agonists could be prevention of internalization of those receptors due to the interaction between ultra-low dose naltrexone and Filamin A affecting the Filamin A, β-arrestin complex required for internalization. As a possible mechanism, it is proposed that ultra-low dose naltrexone, naloxone, and similar mu opioid antagonists co-administered with (a) dopamine D2 and/or dopamine D3 agonists and partial agonists, (b) a drub increasing synthesis of dopamine, e.g. L-DOPA, (c) a drug releasing dopamine, e.g. amphetamine, (d) a drug blocking reuptake of dopamine, e.g. methylphenidate, or (e) a drug decreasing the metabolic degradation of dopamine in the brain (e.g. selegeline) will prevent desensitization of dopamine D2 and D3 receptors following chronic administration of these drugs. It is further proposed that ultra-low doses of naltrexone, naloxone and similar mu opioid receptor antagonists will prevent desensitization of the calcium sensing receptor, the mGluR4, 5, 7 and 8 receptors, the muscarinic M1 receptor, and the calcitonin receptor following chronic administration of agonists of partial agonists at these G protein coupled receptors by similar mechanisms.

In addition to the prevention of internalization of the above mentioned receptors, a second possible mechanism for prevention and/or reversal of desensitization of these receptors may involve the prevention of a switch in second messenger signaling from $G_{\alpha i}$ and $G_{\alpha o}$ to $G_s$. For example, desensitization of mu opioid receptors has been associated with such a switch in G protein second messenger signaling which occurs with repeated administration of opioid agonists. It has been proposed that binding of ultra-low dose naltrexone and naloxone at the pentapeptide site near the carboxy terminal of Filamin A prevents the opioid induced switch in G protein coupling from $G_{\alpha i}$ to $G_s$, and that prevention of this switch in G protein coupling is a mechanism blocking the desensitization of the mu opioid receptor. The D3 receptor and the muscarinic M1 agonist can signal using $G_{\alpha i}$ or $G_s$. The dopamine D2 and mGluR III type receptors, i.e. 4, 6, 7, and 8, also interacts with Filamin A and signals through $G_{\alpha i}$ to inhibit adenyl cyclase.

It has been proposed that loss of therapeutic effects of dopamimetics and augmentation of symptom severity with chronic dopamimetic therapy in RLS may be due to a predominance of dopamine D1 signaling relative to D2/3 signaling. In the baseline state, the dopamine D3 and D2 receptors predominantly signal via $G_{\alpha i}$ and the net effect of receptor activation is inhibition of adenyl cyclase. Dopamine D1 receptor stimulation produces stimulation of adenyl cyclase via $G_s$ second messenger signaling and stimulation of adenyl cyclase.

It is proposed that with continued administration of dopamine D3/D2 receptor agonists and/or drugs elevating extracellular dopamine levels, the dopamine D3, and likely the D2, receptor switch G protein signaling from predominantly $G_{\alpha i}$ to predominantly $G_s$ mediated, resulting in activation of adenyl cyclase. Such switching produces second messenger signaling effects appearing as desensitization of the dopamine D3, and likely D2, receptors and apparent dopamine D1 receptor predominance. Such changes in D2/3 Second messenger signaling may contribute to loss of therapeutic effects of dopamine D2/3 agonists and partial agonists and augmentation of symptom severity in subjects with RLS. Similar switching of G protein coupling is believed to occur in GPCR's that interact with Filamin A and signal through $G_{\alpha i}$ inhibit adenyl cyclase which it is postulated will be a second mechanism of desensitization of these receptors, i.e. muscarinic M1, and mGLuR4, 7, and 8 receptors.

In support of a non-opioid mechanism by which ULD mu opioid receptor antagonist affects dopamine desensitization, studies of the effects of ultra-low dose natrexone in a chronic pain model in intact rodents show no effect of ultra-low dose naltrexone in the absence of exogenously administered opioid agonists. Therefore, ultra-low dose naltrexone appears not to directly affect mu opioid receptor function in the absence of exogenous opioid agonist administration. The principal effect of ultra low dose naltrexone appears to be a prevention of desensitization of the mu opioid receptor only with the administration of exogenous opioid agonists.

Given the lack of effect of ultra-low dose naltrexone on mu opioid receptor function in the absence of an opioid agonist, the effects of ultra low dose naltrexone, naloxone and other opioid antagonists when coadministered with dopamine D2 or D3, muscarinic M1, mGluR4, 5, 7 or 8, calcium sensing, or calcitonin receptor agonists or partial agonists is more likely mediated by direct effects on the function of these receptors and not to indirect effects resulting from mu opioid mediated neurotransmission. As a result, these compounds may produce therapeutic effects in psychiatric and neurological disorders including, but not limited to, RLS, Parkinson's Disease, depression, attention deficit disorder, schizophrenia, Alzheimer's Disease, and psychostimulant drug abuse, therapeutic effects that are not attributable to opioid effects.

These actions of ultra-low dose naltrexone, naloxone, and similar compounds, alone or in combination with the administration of dopamine D2/3 agonists, or partial agonists or drugs which increase extracellular dopamine levels offer new and improved therapeutic properties for the treatment of Restless Let Syndrome, Parkinson's Disease, depression, schizophrenia, attention deficit disorder, and psychostimulant drug abuse and other disorders where dopamine augmentation is desired.

A. Dopamine-Based Movement Disorders

In one aspect, co-administration of an ultra-low dose opioid receptor antagonist with a dopamine agonist and/or a drug enhancing extracellular dopamine levels may have advantageous effects in the treatment or management of dopamine-based movement disorders such as Restless Leg Syndrome and Parkinson's disease.

1. Restless Leg Syndrome (RLS)

Co-administration of an ultra-low dose opioid receptor antagonist with a dopamine agonist has advantageous effects in the treatment of RLS. As detailed in Example 1, a clear reversal of desensitization of pramipexole and ropinirole therapeutic effects (i.e., D2 and D3 agonists) has been observed in the treatment of RLS when an oral ultra-low dose of naltrexone (0.15 µg) was administered along with these dopamimetics.

For RLS treatment, typical doses of pramipexole and ropinirole are about 0.125 mg to about 1.5 mg and 0.25 to 3.0 mg, respectively, taken orally an hour before sleep. The advantageous effects of co-administration of naltrexone (0.15 µg) included earlier onset of action of the dopamimetic, prolongation of therapeutic effects, and an absence of "wearing off" otherwise manifesting as early morning restlessness.

In RLS, chronic treatment with dopamine D2 and D3 agonists can lead to the need for higher doses to maintain therapeutic effects as well as early "wearing off" of drug effects manifest as early morning restlessness. These effects are believed to be due to receptor desensitization. Co-administration of ultra-low dose maltrexone, naloxone, or other opioid receptor antagonist with a dopamine D2 and/or D3 receptor agonist will produce, it is expected, an earlier onset of action of the dopamimetic, prolongation of therapeutic effects, and an absence of "wearing off" otherwise manifesting as early morning restlessness. Examples of dopamine D2 and/or D3 agonists used to treat RLS include, but are not limited to, pramipexole, ropinirole, bromocriptine, and sumanirole.

In one embodiment, receptor stabilization may be achieved by co-administration of naltrexone, in a dose between about 0.01 ng/kg and about 1.5 μg/kg with a dopamine D2 and/or De receptor agonist, to maintain and enhance the therapeutic effects of dopamine D2 and/or D3 receptor agonist. Naltrexone may more preferably be co-administered in a dosage range between 0.01 ng/kg and about 150 ng/kg in certain embodiments. For some patients, the ultra-low dose naltrexone and dopamine receptor agonist may be co-administered in a single dose every night. For patients experiencing RLS symptoms during the daytime, the ultra-low dose naltrexone and dopamine receptor agonist may be co-administered 2 or 3 times daily. Other dosing schedules are possible.

2. Parkinson's Disease

In Parkinson's Disease, dopamine D2 and or D2/3 agonists, monoamine oxidase inhibitors (MAOi) catechol-O-methyl transferase inhibitors (COMTi), and L-DOPA formulations, either separately or together have been shown to be therapeutically efficacious. The dopamine D2 and D2/3 agonists include, but are not limited, to pramipexole, ropinirole, bromocriptine, sumanirole, and pergolide. The side effects of "wearing off" and "on-off" periods, as well as loss of therapeutic efficacy of these agents, have been reported with these drugs. These effects are believed to be mediated by desensitization of dopamine D2 and D3 receptors.

In one embodiment, a treatment method includes co-administration of ULD naltrexone, naloxone, or other opioid receptor antagonist with a dopamine D2 and/or D3 receptor agonist, alone or combination with an L-DOPA formulation, with an L-DOPA formulation plus a COMTi, with an L-DOPA formulation plus an MAOi, or with an L-DOPA formulation plus an MAOi and COMTi to prevent receptor desensitization. In another embodiment, a treatment method includes co-administration of ULD naltrexone, naloxone, or other opioid receptor antagonist with an L-DOPA formulation, with an L-DOPA formulation plus a COMTi, with an L-DOPA formulation plus an MAOi, or with an L-DOPA formulation plus an MAOi and a COMTi to prevent receptor desensitization. Typical doses of SINEMET used to treat Parkinson's Disease are 1 tablet SINEMET 25/100 TID taken orally or up to 15 tablets SINEMET 25/100 taken orally daily in divided doses. Typical doses of pramipexole used to treat Parkinson's Disease range beam 0.125 mg TID orally to 1.5 mg TID orally. The typical doses of REQUIP used to treat Parkinson's Disease range from 0.25 mg TID orally to 24 mg per day taken orally in three divided doses. However, escalation of does with repeated administration of pramipexole and ropinirole, which is frequently seen, will be prevented when dopamine augmenting drugs are co-administered with an ultra-low dose of naltrexone, naloxone, or other opioid antagonist.

In one embodiment, receptor stabilization is achieved by co-administration of naltrexone in a dose between about 0.01 ng/kg and about 1.5 μg/kg with a dopamine D2 and/or D3 receptor agonist, separately or in further combination with an L-DOPA formulation. In still another embodiment, naltrexone is co-administered in a dose between about 0.01 ng/kg and about 1.5 μg/kg with an L-DOPA formulation. In certain embodiments, naltrexone is co-administration in a dosage range between 0.01 ng/kg and about 150 ng/kg. Such co-administration would maintain and enhance the therapeutic effects of the dopamine D2 and/or D3 receptor agonist, the L-DOPA formulation, or both Compositions and unit dose formulations comprising such active agent combinations may be provided for the treatment of Parkinson's Disease.

B. Depression, Refractory Depression

Dopamine D2 and/or D3 receptor agonists, as well as drugs increasing extracellular dopamine levels, have been used both separately and in conjunction with other antidepressant drugs to treat unipolar and bipolar depression. Chronic administration of dopamine D2 and/or D3 receptor agonists and partial agonists have been shown to produce receptor desensitization, which decreases the therapeutic effects of these drugs. Examples of dopamine D2 and/or D3 receptor agonists and partial agonists and drugs increasing extracellular dopamine levels include, but are not limited to, pramipoxole, ropinirole, aripiprazole, sumanirole, methylphenidate formulations (both in immediate and delayed release forms, including selective enantiomers), and amphetamine formulations, in both immediate and delayed release form, including selective enantiomers; bupropion; the serotonin dopamine reuptake inhibitor sertraline, serotonin norepinephrine reuptake inhibitors such as duloxeline, venlaxafine or desvenlafaxine, triple uptake inhibitors (serotonin norepinephrine dopamine) such as JNJ 7925476, tesofensine, and DOV 216303, dopamine reuptake inhibitors, as well as drugs decreasing dopamine metabolism including but not limited to phenelzine, tranylcypromine, selegiline, rasagiline and tolcapone are believed to rely, at least partially, on dopamine augmentation as a mechanism for their anti-depressant effects.

In one embodiment, treatment methods are provided that include co-administration of ultra-low dose naltrexone, naloxone, or other opioid receptor antagonist in combination with (i) a dopamine D2 and/or D3 receptor agonist or partial agonist, (ii) a drug that increases extracellular dopamine levels, (iii) an MAOi inhibitor (iv) a dopamine and norepinephrine reuptake inhibiting antidepressant, (v) a serotonin and dopamine reuptake inhibiting antidepressant, (vi) a serotonin norepinephrine reuptake inhibiting antidepressant, (vii) a triple uptake (i.e., serotonin and norepinephrine and dopamine) reuptake inhibiting antidepressant, (viii) a dopamine reuptake inhibiting antidepressant to prevent receptor desensitization, or (ix) a combination of the foregoing. Praximpexole has been used at doses of about 0.125 to about 1.5 mg TID taken orally in the treatment of depression. However, co-administration of dopamine augmenting drugs with an ultra-low dose of naltrexone, naloxone or other opioid receptor antagonist should prevent dose escalation and loss of therapeutic effects. In one embodiment, receptor stabilization is achieved by co-administration of naltrexone in a dose between about 0.01 ng/kg and about 1.5 μg/kg in combination with (i) a dopamine D2 and/or D3 receptor agonist or partial agonist, (ii) a drug that increases extracellular dopamine levels, (iii) an MAOi, (iv) a dopamine and norepinephrine reuptake inhibiting antidepressant, (v) a serotonin and dopamine reuptake inhibiting antidepressant, (vi) a serotonin norepinephrine reuptake inhibiting antidepressant, (vii) a triple uptake (i.e. serotonin, norepinephrine, and dopamine) reuptake inhibiting antidepressant, (viii) a dopamine reuptake inhibiting antidepressant, or (ix) a combination thereof. In certain embodiments, naltrexone is co-administered in a dosage range between 0.01 ng/kg and about 150 ng/kg. Such treatment may maintain and enhance the therapeutic effects of dopamine D2 and/or D3 receptor agonists and partial agonists, a drug that increase extracellular dopamine levels, and MAOi, a dopamine and norepinephrine reuptake inhibiting antidepressant, a serotonin and dopamine reuptake inhibiting antidepressant, a serotonin norepinephrine reuptake inhibiting antidepressant, a triple uptake (i.e. serotonin, norepinephrine, and dopamine) reuptake inhibiting antidepressant, or a dopamine reuptake inhibiting antidepressant. Compositions and unit dose formulations comprising such active agent combinations may be provided for the treatment of depression.

C. Schizophrenia

Partial agonists for the dopamine D2 and/or D3 receptors have therapeutic benefits in schizophrenia and bipolar depression upon initial treatment, but often demonstrate a loss of efficacy with repeated administration. These partial agonists include, but are not limited to drugs such as preclamol, terguride, talipexole, roxindole, rotigitine, SDZ-208-911, SDZ 208-912, bifeprunox, PD 158771, PD 128483, aripiprazole, aplindore, BP897, and CJB090. A likely mechanism for the observed loss of efficacy is receptor desensitization. Preclamol has been used in a dose of 300 mg BID taken orally and shown to have antipsychotic effects; in addition, a dose range of 100 mg to 1,000 mg preclamol taken orally BID is proposed. Typical doses of aripiprazole used to treat schizophrenia are from 10 mg to 40 mg per day taken orally. Loss of therapeutic effects with subsequent dose escalation and/of reversal of dose escalation may be achieved when these drugs are co-administered with an ultra-low dose naltrexone, naloxone, or other opioid receptor antagonist. Drugs that elevate extracellular DA levels have been shown to produce symptomatic improvements in schizophrenic subjects who are being treated with symptoms and to improve cognition in schizophrenic subjects who are being treated with neurologic drugs which block a sufficient level of DA D2 receptors to control positive symptoms. These drugs include, but are not limited to, amphetamine and amphetamine formulations, and methylphenidate and methylphenidate formulations.

The co-administration of ultra-low dose naltrexone, naloxone, or other opioid receptor antagonist, in combination with a dopamine D2/D3 partial agonists, D2 partial agonists, or D3 partial or full agonists may be useful to prevent dopamine D2 and D3 receptor desensitization. In one embodiment, receptor stabilization is achieved by co-administration of naltrexone in a dose between about 0.01 ng/kg and about 1.5 µg/kg with a dopamine D2/3 or D2 partial agonist, or a D3 partial or full agonist. In certain embodiments, naltrexone is co-administered in a dosage range between 0.01 ng/kg and about 150 ng/kg. Such treatment may maintain and enhance the therapeutic effects of the dopamine D2/3 or D2 partial agonist, or the D3 partial or full agonist, or a drug increasing extracellular dopamine levels. Compositions and unit dose formulations comprising such active agent combinations may be provided for the treatment of schizophrenia.

D. Psychostimulant Abuse

Dopamine D2 and/or D3 receptor partial agonists and drugs which increase extracellular dopamine levels have been shown in animal models of psychostimulant abuse to decrease drug rewarded self-administration and reduce the reinforcing and addictive properties of psychostimulants including, but not limited to, cocaine, amphetamine, and amphetamine derivatives such as methamphetamine. However, dopamine D2 and/or D3 partial agonists and drugs increasing extracellular dopamine levels can produce desensitization of dopamine D2 and/or D3 receptors with repeated dosing, limiting the utility of these drugs for extended treatment of psychostimulant abuse. In addition, it has been proposed that selective dopamine D3 full and partial agonists and selective dopamine D2 partial and full agonists will similarly decrease drug rewarded self-administration, reduce the reinforcing and addictive properties of psychostimulant drugs, and produce desensitization of dopamine D3 and/or D2 receptors with repeated administration. Full dopamine D2 and D3 agonists may be preferentially given via an oral route or by a slow release method to allow a gradual rise in brain levels of these drugs thus minimizing the potential subjective effects of full agonists. Examples of these drugs include, but are not limited to, BP897, CJB 090, RGH 237, pramiprexole, ropinirole, preclamol, terguride, aripiprazole, methylphenidate, and amphetamine.

This loss of therapeutic effect seen with desensitization of the dopamine D3 and/or D2 receptor(s) following repeated dosing with dopamine D3 and/or D2 receptor agonists and partial agonists, as well as with drugs elevating extracellular dopamine levels, are prevented or reversed by co-administration of an ultra-low dose of maltrexone, naloxone, or other opioid receptor antagonist. Selective dopamine D3 partial and full agonist compounds are characterized by selective and high affinity for dopamine D3 receptors, demonstrate inhibition of forskolin-induced cyclic AMP accumulation, and increase mitogenesis in cells expressing the dopamine D3 receptor with an efficacy similar to that seen with dopamine and other full dopamine D3 agonists. It is expected that these effects would be selectively reversed in cells expressing dopamine D3 receptors by dopamine D3 selective antagonists such as nafadotride and similar compounds.

In one embodiment, the dose of methylphenidate used to treat methamphetamine abuse is 54 mg/day of a slow release methylphenidate preparation. In accordance with the present disclosure, co-administration of ultra-low dose naltrexone, naloxone, or a similar compound in combination with a dopamine D3 and/or D2 receptor partial or full agonist, a dopamine reuptake inhibitor (such as methylphenidate) or a dopamine releasing drug (such as an amphetamine formulation) may be used to prevent dopamine D3 and/or D2 receptor desensitization. In one embodiment, receptor stabilization is achieved by co-administration of naltrexone in a dose between about 0.01 ng/kg and about 1.5 µg/kg with a dopamine D3 and/or D2 partial agonist and with drugs which elevate extracellular dopamine levels. In certain embodiments, naltrexone is co-administered in a dosage range between 0.01 ng/kg and about 150 ng/kg. Such treatment may prevent the desensitization seen with repeated administration, creating a novel composition for the treatment of psychostimulant abuse.

E. Attention Deficit Hyperactive Disorder (ADHD)

In another embodiment the use of an ultra-low dose of naltrexone, naloxone, or other opioid receptor antagonist is provided in combination with a drug that enhances dopaminergic neurotransmission by increasing extracellular dopamine levels, for the treatment of attention deficit hyperactivity disorder. Decreased phasic dopamine release is believed to be an important deficit in ADHD. Exemplary agents for coformulation include, but are not limited to, a methylphenidate formulation (either in immediate or delayed release form, including selective enantiomers), an amphetamine formulation (in either an immediate or delayed release form, including selective enantiomers), or a norepinephrine transporter inhibitor such as atomoxetine, all of whose actions are believed to be mediated by augmentation of extracellular dopamine levels, as well as other drugs enhancing dopaminergic neurotransmission.

Typical doses of ADDERALL™, an amphetamine preparation, range from a daily dose of 2.5 mg per day up to doses 30 mg given twice a day orally. Typical doses of CONCERTA™ range from 18 mg/day to 72 mg/day, generally not to exceed 2 mg/kg/day. Typical doses of RITALIN™ (methylphenidate) tablets are 10 to 60 mg/day given twice or three times per day; higher doses have been used. Typical doses of atomoxetine are 0.5 mg/kg to 1.4 mg/kg taken twice dally orally up to a maximum of a 100 mg dally dose. However, lower doses should be effective, when co-administered with an ultra-low dose of naltrexone, naloxone, or other opioid receptor antagonist.

In one embodiment, receptor stabilization is achieved by co-administration of naltrexone in a dose between about 0.01 ng/kg and about 1.5 µg/kg with a drug which increases extracellular dopamine levels to treat ADHD. In certain embodiments, naltrexone is co-administered in a dosage range between 0.01 ng/kg and about 150 ng/kg. Such treatment may maintain the therapeutic effects of the drug which increases extracellular dopamine levels. Compositions and unit dose formulations comprising such active agent combinations may be provided for the treatment of ADHD.

A distinct benefit of ultra low dose opioid antagonists stabilizing dopamine augmentation in treatment of ADHD would be the prevention of dose escalation and so allow use of lower doses of agents such as amphetamine salts and methylphenidate, which would minimize the known cardiovascular risks of arrhythmias, hypertension and and/or tachycardia linked to an elevated lifetime probability of myocardial infarction and stroke.

F. Other Disorders

Other disorders involving dopamine receptors or extracellular dopamine levels may be treated in accordance with the present disclosure. As with the specific disorders described herein, other disorders may benefit from the use of ultra-low dose naltrexone (or other opioid receptor antagonist) combined with agents that result in agonist or partial agonist actions on dopamine receptors or that increase extracellular dopamine levels. Specifically, prevention of dose escalation due to desensitization of dopamine D2 and/or D3 receptors should allow lower doses of these drugs that augment dopaminergic neurotransmission, and the "wearing off" or "on-off" withdrawal side-effects will be diminished.

In another embodiment, an ultra low dose naltrexone (or other opioid receptor antagonist) combined a dopamimetic is used in the treatment of pituitary adenomas. Many pituitary adenomas, including but not limited to prolactin secreting adenomas, nonfunctioning adenomas, and adenomas secreting ACTH, have membrane expressed dopamine D2 receptors. Agonist stimulation of these receptors inhibits secretion of hormones by such adenomas, thus decreasing symptoms produced by excessive hormone secretion from these adenomas. This frequently leads to shrinkage of adenomas, thereby sparing the patient the need for surgery of radiation therapy. Such adenomas are treated with dopamine D2 agonists such as bromocriptine, typical doses of 2.5 mg twice daily up to 30 mg daily in divided doses, or cabergoline, typical doses of 0.25 mg to 3 mg weekly. Not all such tumors demonstrate an adequate therapeutic response to dopamine agonist therapy. The combination of ultra low dose naltrexone (or other opioid receptor antagonist) at 0.01 ng/kg to 1.5 µg/kg orally daily or depot injection, 0.01 ng/kg to 10 µg/kg, co-administered with such dopamine agonist therapy will prevent desensitization of pituitary dopamine D2 receptors, allowing a larger fraction of such tumors to be successfully treated and/or to be treated at lower doses of dopamine agonists resulting in lesser treatment related side effects.

In yet another embodiment, an ultra low dose naltrexone (or other opioid receptor antagonist) combined a dopamimetic is used in the treatment of obesity and the metabolic syndrome which accompanies obesity including insulin resistance and type II diabetes. Studies in humans have shown that bromocriptine, a dopamimetic, at a dose of 2.5 mg reduces leptin, insulin, and glucose levels in obese female human subjects and improves glycemic control in type II diabetics. Genetic studies have shown genetic polymorphisms of the dopamine D3 receptor which produce lesser levels of dopamine D3 signaling are more commonly seen in obese adults particularly those with binge eating disorders. Imaging studies have suggested that decreased dopamine D2 signaling in obese subjects. Animal studies have shown that bromocriptine administered to leptin deficient animals reduces hyperphagia and adiposity. Animal studies have shown that dopamine D2 receptor agonists can ameliorate type II diabetic changes in obese animals. Ultra low dose naltrexone for other opioid receptor antagonist) in combination with dopamine D2 and D3 agonists and partial agonists including but not limited to bromocriptine will enhance the metabolic effects of such dopamimetics by preventing desensitization of dopamine D2 and D3 receptors with chronic treatment. Co-administration of naltrexone in a dose between about 0.01 ng/kg and about 1.5 µg/kg with a dopamimetic may be used to beat obesity, the metabolic syndrome and type II diabetes. In certain embodiments, naltrexone is co-administered in a dosage range between about 0.010 ng/kg and about 150 ng/kg.

In other embodiments, ultra-low doses of mu opioid receptor antagonists, such as naltrexone and naloxone, may be co-administered with agonists of the calcium sensing receptor, the mGluR4, 5, 7 and 8 receptors, the muscarinic M1 receptor, or the calcitonin receptor to prevent the desensitization of the receptors. Co-administration of these agonists with ultra-low dose opioid antagonists likely will prevent desensitization of those receptors and augment agonists effects for each of these receptors.

Accordingly, in some embodiments, the ultra-low dose opioid receptor antagonist may be co-administered with agonists or partial agonists or other drugs that directly or indirectly effect the calcitonin receptors, calcium sensing receptors, metabotropic glutamatergic receptors or muscarinic cholinergic receptors. In certain embodiments, the ultra-low dose opioid receptor antagonist may be co-administered with drugs that directly or indirectly effect muscarinic receptors, particularly the M1 muscarinic receptor. In certain embodiments, the ultra-low dose opioid receptor antagonist may be administered to prevent or reduce desensitization effects in conjunction with cognitive enhancement treatments, such as in the treatment of Alzheimer's Disease and to treat cognitive deficits in other disorders such as schizophrenia.

For example, the ultra-low dose opioid receptor antagonist may be co-administered with an M1 muscarinic cholingergic agonist or partial agonist drug or with acetylcholinesterase inhibitors which increase the extracellular levels of acetylcholine in patient with Alzheimer's Disease and in patients with cognitive impairments due to other disorders such as schizophrenia. In Alzheimer's Disease, particularly in mild to moderate Alzheimer's Disease, there is a loss of acetylcholine neurons in brain which is believed to mediate cognitive deficits such as memory loss. Administration of acetylcholinesterase inhibitors such galantamine (Reminyl, Razadyne), donepezil (Aricept), and rivastigmine (Exelon) to subjects with mild to moderate Alzheimer's Disease produces improvements in cognitive function by increasing extracellular acetylcholine levels. It is believed that M1 muscarine cholinergic receptors mediate a substantial part of the cognitive improvement seen with acetylcholinesterase inhibitors. Typical doses of galantamine are less than 24 mg/day, typical doses of donepezil are 5-10 mg/day, and typical doses of rivastigmine are 1.5-6.0 mg taken twice daily. These improvements in cognitive function, however, decrease with time. While part of this loss of therapeutic effects may be due to progression of Alzheimer's Disease, desensitization of the M1 muscarinic cholingergic receptor with continued use of these medications is believed to mediate another part of this loss of therapeutic function.

In one embodiment, M1 muscarinic cholingergic receptor stabilization is achieved by co-administration of naltrexone in a dose between about 0.01 ng/kg and about 1.5 µg/kg with a drug which increases extracellular acetylcholine levels or with an M1 cholinergic agonist or partial agonist to treat Alzheimer's Disease. In certain embodiments, naltrexone is co-administered in a dosage range between 0.01 ng/kg and about 150 ng/kg. Such treatment may maintain the therapeutic effects of the drug which increases extracellular acetylcholine levels. Compositions and unit dose formulations comprising such active agent combinations may be provided for the treatment of Alzheimer's Disease.

The present methods and compositions can be further understood and illustrated by the following non-limiting examples.

Example 1

In an open-label trial, five subjects diagnosed with RLS treated with either pramipexole of mirapex who had experienced at least one episode of dose escalation due to loss of therapeutic effects at an initially therapeutic dose participated in three phases of testing, with each phase lasting five nights. PAM-RL ankle monitors (Philips Respironics) were utilized to count Periodic Limb Movements (PLMs), a measurement that is resistant to placebo effects.

During Phase 1, the subjects were administered 50% the subjects' clinical "full" dosage of pramipexole or ropinirole. In this Phase, an average of 19.5 PLMs per hour (range 10.1-32.8) were observed, indicating unsatisfactory treatment of RLS. During Phase 2, the subjects were co-administered 50% the subject's normal dosage of pramipexole or ropinirole along with ultra-low dose naltrexone (0.15 µg). In Phase 2, an average of 9.1 PLMs per hour were observed. During Phase 3, the objects were administered 100% the subjects' normal dosage of pramipexole or ropinirole alone. In Phase 3, an average of 8.5 PLMs were observed (range 2.8-17.8) not significantly different from Phase 2. The results of the trial are illustrated in FIG. 1.

When PLMs are normalized to the level seen in each subject during Phase 1, the results indicate that the addition of 0.15 µg naltrexone to ultra low dose naltrexone lowers PLMs per hour by an average of 53% which is highly statistically significant even in this small cohort ($P=0.006$, 2 tailed t-test). Full dose pramipexole or ropinirole (Phase 3) produced a 63% decrease in PLMs; this was not statistically significantly different from the level of PLMs seen with half dose pramipexole or ropinirole plus 0.015 µg naltrexone ($P=0.07$, 2 tailed t-test). The normalized results of the test data are illustrated in FIG. 2.

Ultra low dose naltrexone in combination with half the usual dose of pramipexole or ropinirole therefore advantageously reversed the loss of therapeutic effects due to desensitization of dopamine D2 and D3 receptor signaling seen with chronic dosing.

Example 2

Figure 3:
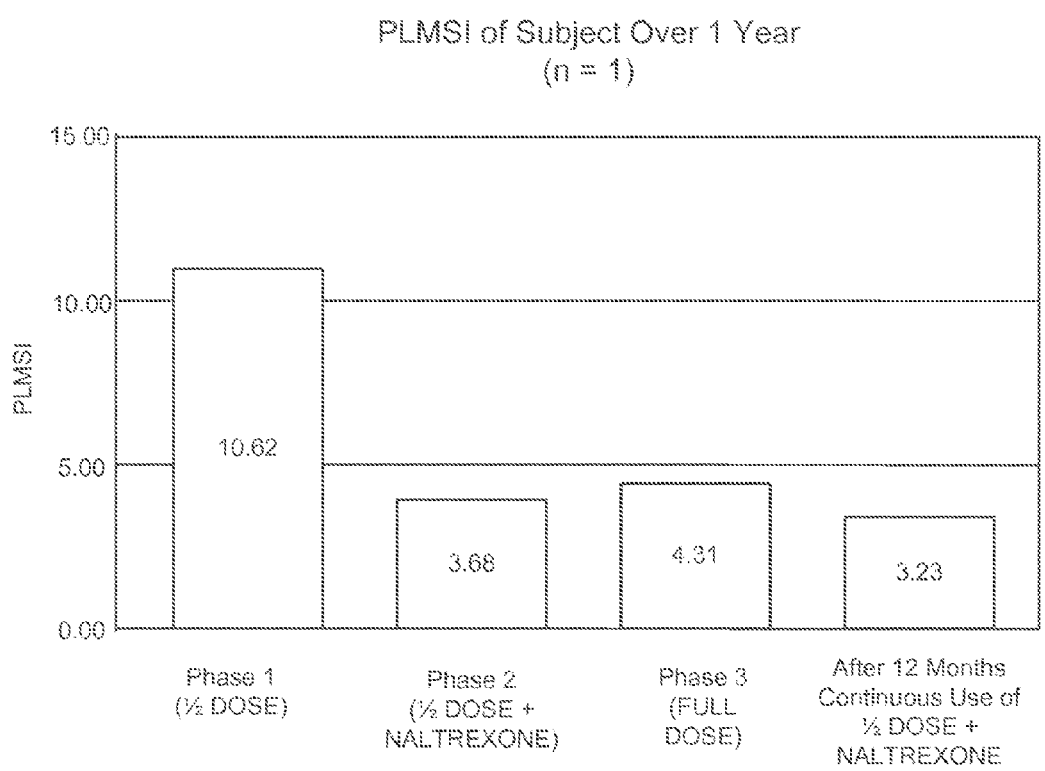
FIG. 3 is bar graph, illustrating the number of PLMs observed in a subject during an initial 3 phase trial and following a one-year trial in which the subject maintained treatment on half dose dopamimetic (pramipexole) plus ultra-low dose naltrexone.

One subject of the initial 3 phase trial has now been maintained on half the previous dose of pramipexole plus 0.15 µg naltrexone for a year. Monitoring this subject for PLMs for five nights showed no loss of therapeutic effects, i.e. no evidence of tachyphylaxis, over this period. The subject's PLMSI after 12 months of co-administration therapy was 3.23, indicating an effective treatment of RLS. The subject did not exhibit any evidence of desensitization to the co-administration therapy over the 12 month trial. The results of the initial 3 phase trial and after 12 month treatment of the co-administration therapy are illustrated in FIG. 3.

Publications cited herein are incorporated by reference. Modifications and variations of the methods and devices described herein will be obvious to those skilled in the art from the foregoing detailed description. Such modifications and variations are intended to come within the scope of the appended claims.

We claim:

1. A method for treating Restless Leg Syndrome (RLS) comprising administering to a patient in need thereof:
   a dopamine receptor agonist or partial agonist; and
   an opioid receptor antagonist in an ultra-low dose amount, wherein the dopamine receptor agonist or partial agonist is administered in an amount that is therapeutically effective when co-administered with the opioid receptor antagonist in an ultra-low dose amount.

2. The method of claim 1, wherein the opioid receptor antagonist is selected from naloxone, naltrexone, diprenorphine, etorphine, dihydroetorphine, and combinations thereof.

3. The method of claim 1, wherein the dopamine receptor agonist or partial agonist is selected from pramipexole, ropinirole, bromocriptine, pergolide, preclamol, talipexole, roxindole, rotigotine, SDZ 208-911, SDZ 208-912, bifeprunox, aripiprazole, PD 158771, PD128483, N-propylnorapomorphine, apomorphine, sumanirole, aplindore, BP897, CJB090, RGH237, and combinations thereof.

4. The method of claim 1, wherein the ultra-low dose amount of the opioid receptor antagonist is between about 0.01 ng/kg and about 1.5 µg/kg.

5. The method of claim 1, wherein the ultra-low dose amount of the opioid receptor antagonist is between about 0.01 ng/kg and about 150 ng/kg.

6. A method for treating Restless Leg Syndrome (RLS) comprising administering to a patient in need thereof pramipexole and/or ropinirole and naltrexone in an ultra-low dose amount.

7. The method of claim 6, wherein the ultra-low dose amount of the naltrexone is between about 0.01 ng/kg and about 1.5 µg/kg.

8. The method of claim 6, wherein the ultra-low dose amount of the naltrexone is between about 0.01 ng/kg and about 150 ng/kg.

9. A method for treating Restless Leg Syndrome (RLS), comprising administering naltrexone in an ultra-low dose amount to an RLS patient undergoing treatment with pramipexole and/or ropinirole.

10. The method of claim 9, wherein the ultra-low dose amount of naltrexone is between about 0.01 ng/kg and about 1.5 µg/kg.

11. The method of claim 6, wherein the ultra-low dose amount of naltrexone is between about 0.01 ng/kg and about 150 ng/kg.

* * * * *